US007189753B1

(12) United States Patent
Cady et al.

(10) Patent No.: US 7,189,753 B1
(45) Date of Patent: *Mar. 13, 2007

(54) PREEMPTIVE PROPHYLAXIS OF MIGRAINE

(76) Inventors: Roger K. Cady, 631 Riverview Rd., Ozark, MO (US) 65721; Donna Lee Gutterman, c/o Glaxo Wellcome Inc. Five Moore Dr., P.O. Box 13398, Research Triangle Park, NC (US) 27709-3398; Stephen Venson O'Quinn, c/o Glaxo Wellcome Inc. Five Moore Dr., P.O. Box 13398, Research Triangle Park, NC (US) 27709-3398

( * ) Notice: Subject to any disclaimer, the term of this patent is extended or adjusted under 35 U.S.C. 154(b) by 0 days.

This patent is subject to a terminal disclaimer.

(21) Appl. No.: 09/575,277

(22) Filed: May 22, 2000

Related U.S. Application Data

(63) Continuation-in-part of application No. PCT/US99/09414, filed on Apr. 29, 1999, which is a continuation-in-part of application No. 09/185,310, filed on Nov. 3, 1998, now Pat. No. 6,066,092.

(60) Provisional application No. 60/064,879, filed on Nov. 6, 1997.

(51) Int. Cl.
 A61K 31/405 (2006.01)
 A61K 31/335 (2006.01)
 A61K 31/34 (2006.01)

(52) U.S. Cl. ............... 514/415; 514/449; 514/461; 514/473; 600/300

(58) Field of Classification Search .......... 514/415, 514/449, 461, 473; 600/300
 See application file for complete search history.

(56) References Cited

U.S. PATENT DOCUMENTS

| 4,305,502 | A | 12/1981 | Gregory et al. |
| 4,371,516 | A | 2/1983 | Gregory et al. |
| 4,758,598 | A | 7/1988 | Gregory |
| 4,816,470 | A | 3/1989 | Dowle et al. |
| 4,997,841 | A | 3/1991 | Oxford et al. |
| 5,037,845 | A | 8/1991 | Oxford |
| 5,288,748 | A | 2/1994 | Wikstrom et al. |
| 5,298,520 | A | 3/1994 | Baker et al. |
| 5,317,103 | A | 5/1994 | Baker et al. |
| 5,382,592 | A | 1/1995 | Gylys et al. |
| 5,385,928 | A | 1/1995 | Flaugh |
| 5,387,593 | A | 2/1995 | Mattson et al. |
| 5,418,236 | A | 5/1995 | Carmosin et al. |
| 5,433,915 | A | 7/1995 | Yamamoto et al. |
| 5,451,584 | A | 9/1995 | Baudy et al. |
| 5,466,688 | A | 11/1995 | Commons et al. |
| 5,466,699 | A | 11/1995 | Robertson et al. |
| 5,468,768 | A | 11/1995 | Cipollina et al. |
| 5,519,025 | A | 5/1996 | Yardley et al. |
| 5,545,644 | A | 8/1996 | Macor et al. |
| 5,554,639 | A | 9/1996 | Craig et al. |
| 5,602,128 | A | 2/1997 | Baudy et al. |
| 5,602,162 | A | 2/1997 | Baker et al. |
| 5,618,948 | A | 4/1997 | Borrett et al. |
| 5,637,611 | A | 6/1997 | King et al. |
| 5,705,520 | A | 1/1998 | Craig et al. |
| 5,837,715 | A | 11/1998 | Pineiro et al. |
| 5,840,018 | A | 11/1998 | Michaeli |
| 5,852,049 | A * | 12/1998 | Perez et al. ............... 514/415 |
| 5,863,559 | A | 1/1999 | Phillips et al. |
| 5,872,145 | A * | 2/1999 | Plachetka ................. 514/415 |
| 6,048,850 | A | 4/2000 | Young et al. |
| 6,060,499 | A * | 5/2000 | Plachetka ................. 514/415 |
| 6,066,092 | A * | 5/2000 | Cady et al. ............... 600/300 |
| 6,586,458 | B1 * | 7/2003 | Plachetka ................. 514/415 |
| 2001/0004644 | A1 * | 6/2001 | Levin ....................... 514/646 |

FOREIGN PATENT DOCUMENTS

| DE | 42 26 527 | 2/1994 |
| DE | 44 14 113 | 10/1995 |
| EP | 0 147 107 | 7/1985 |
| EP | 0 225 726 | 6/1987 |
| EP | 0 237 678 | 9/1987 |
| EP | 0 242 939 | 10/1987 |
| EP | 0 244 085 | 11/1987 |
| EP | 0 254 433 | 1/1988 |
| EP | 0 303 506 | 2/1989 |

(Continued)

OTHER PUBLICATIONS

Hyperdictionary, AUra definition(see webster's 1913 dictionary).*
Dictionary. LaborLawTalk.com, Definitiona of aura in General, http://dictionary.laborlawtalk.com/aura.*
Online Medical Dictionary, "Aura", http://cancerweb.ncl.ac.uk/cgi-bin/omd?wuery=aura&action-Search+OMD.*
Aura Migraine, a definition of Aura migraine, www.paretnscafe.co.us/aura-migraine/.*
Cady, R.K.: "Diagnosis of Headache" Treating the Headache Patient, Ch. 6, Marcel Dekker, Inc., 1995, pp. 101-122, New York, XP000933674.

(Continued)

*Primary Examiner*—Vickie Kim
(74) *Attorney, Agent, or Firm*—Husch & Eppenberger LLC; H. Frederick Rusche (57) ABSTRACT

A method of preventing the headache phase of migraine in a human comprises administration of a $5HT_1$ receptor agonist or administration of an over-the-counter or nonprescription drug to said human exhibiting prodrome symptoms of migraine. Suitably, the method comprises administration of a migraine headache phase-preventing effective amount of the $5HT_1$ agonist or over-the-counter or nonprescription drug. There is disclosed a preemptive prophylaxis migraine method using the following cognitive tests: Simple Reaction Time; Running Memory Continuous Performance Task; Matching to Sample; Mathematical Processing Task; and interpreting the results as a percent of baseline indicator of need for prophylaxis.

9 Claims, 4 Drawing Sheets

FOREIGN PATENT DOCUMENTS

| | | |
|---|---|---|
| EP | 0 313 397 | 4/1989 |
| EP | 0 354 777 | 2/1990 |
| EP | 0 382 570 | 8/1990 |
| EP | 0 438 230 | 7/1991 |
| EP | 0 450 238 | 10/1991 |
| EP | 0 451 008 | 10/1991 |
| EP | 0 451 022 | 10/1991 |
| EP | 0 464 558 | 1/1992 |
| EP | 0 478 954 | 4/1992 |
| EP | 0 490 689 | 6/1992 |
| EP | 0 494 774 | 7/1992 |
| EP | 0 497 512 | 8/1992 |
| EP | 0 501 568 | 9/1992 |
| EP | 0 503 440 | 9/1992 |
| EP | 0 506 363 | 9/1992 |
| EP | 0 506 369 | 9/1992 |
| EP | 0 580 539 | 1/1994 |
| EP | 0 581 538 | 2/1994 |
| EP | 0 586 866 | 3/1994 |
| EP | 0 590 970 | 4/1994 |
| EP | 0 590 971 | 4/1994 |
| EP | 0 603 432 | 6/1994 |
| EP | 0 610 134 | 8/1994 |
| EP | 0 620 222 | 10/1994 |
| EP | 0 620 223 | 10/1994 |
| EP | 0 639 072 | 2/1995 |
| EP | 0 641 787 | 3/1995 |
| EP | 0 644 187 | 3/1995 |
| EP | 0 645 385 | 3/1995 |
| EP | 0 648 767 | 4/1995 |
| EP | 0 666 258 | 8/1995 |
| EP | 0 668 273 | 8/1995 |
| EP | 0 683 155 | 11/1995 |
| EP | 0 700 905 | 3/1996 |
| EP | 0 703 229 | 3/1996 |
| EP | 0 707 007 | 4/1996 |
| EP | 0 708 102 | 4/1996 |
| EP | 0 712 837 | 5/1996 |
| EP | 0 714 894 | 6/1996 |
| EP | 0 714 896 | 6/1996 |
| EP | 0 729 958 | 9/1996 |
| EP | 0 733 628 | 9/1996 |
| EP | 0 736 525 | 10/1996 |
| EP | 0 747 353 | 12/1996 |
| EP | 0 749 962 | 12/1996 |
| EP | 0 755 932 | 1/1997 |
| EP | 0 768 301 | 4/1997 |
| EP | 0 810 220 | 12/1997 |
| FR | 2 522 175 | 8/1983 |
| FR | 2 672 201 | 8/1992 |
| FR | 2 699 918 | 7/1994 |
| FR | 2 707 294 | 1/1995 |
| FR | 2 737 723 | 2/1997 |
| GB | 2 008 646 | 6/1979 |
| GB | 2 081 717 | 2/1982 |
| GB | 2 082 175 | 3/1982 |
| GB | 2 083 463 | 3/1982 |
| GB | 2 124 210 | 2/1984 |
| GB | 2 150 932 | 7/1985 |
| GB | 2 162 522 | 2/1986 |
| GB | 2 168 347 | 6/1986 |
| GB | 2 168 973 | 7/1986 |
| GB | 2 185 020 | 7/1987 |
| GB | 2 186 874 | 8/1987 |
| GB | 2 191 488 | 12/1987 |
| GB | 2 286 185 | 8/1995 |
| GB | 2 289 464 | 11/1995 |
| GB | 2 289 465 | 11/1995 |
| JP | 5-320157 | 12/1993 |
| JP | 6-41071 | 2/1994 |
| JP | 7-97370 | 4/1995 |
| JP | 7-109265 | 4/1995 |
| WO | 91/18897 | 12/1991 |
| WO | 92/06973 | 4/1992 |
| WO | 92/11013 | 7/1992 |
| WO | 92/11014 | 7/1992 |
| WO | 92/13856 | 8/1992 |
| WO | 93/00086 | 1/1993 |
| WO | 93/00094 | 1/1993 |
| WO | 93/00333 | 1/1993 |
| WO | 94/02460 | 2/1994 |
| WO | 94/02477 | 2/1994 |
| WO | 94/03446 | 2/1994 |
| WO | 94/06789 | 3/1994 |
| WO | 94/10171 | 5/1994 |
| WO | 94/11356 | 5/1994 |
| WO | 94/11363 | 5/1994 |
| WO | 94/13620 | 6/1994 |
| WO | 94/14770 | 7/1994 |
| WO | 94/14771 | 7/1994 |
| WO | 94/14772 | 7/1994 |
| WO | 94/14773 | 7/1994 |
| WO | 94/14779 | 7/1994 |
| WO | 94/15930 | 7/1994 |
| WO | 94/18193 | 8/1994 |
| WO | 94/20466 | 9/1994 |
| WO | 94/21610 | 9/1994 |
| WO | 94/21611 | 9/1994 |
| WO | 94/21619 | 9/1994 |
| WO | 94/24127 | 10/1994 |
| WO | 94/29293 | 12/1994 |
| WO | 95/01334 | 1/1995 |
| WO | 95/01965 | 1/1995 |
| WO | 95/05366 | 2/1995 |
| WO | 95/05381 | 2/1995 |
| WO | 95/05383 | 2/1995 |
| WO | 95/06636 | 3/1995 |
| WO | 95/11903 | 5/1995 |
| WO | 95/14004 | 5/1995 |
| WO | 95/20588 | 8/1995 |
| WO | 95/21166 | 8/1995 |
| WO | 95/21167 | 8/1995 |
| WO | 95/28933 | 11/1995 |
| WO | 95/32196 | 11/1995 |
| WO | 96/04269 | 2/1996 |
| WO | 96/04274 | 2/1996 |
| WO | 96/06638 | 3/1996 |
| WO | 96/06846 | 3/1996 |
| WO | 96/09288 | 3/1996 |
| WO | 96/11195 | 4/1996 |
| WO | 96/11685 | 4/1996 |
| WO | 96/11923 | 4/1996 |
| WO | 96/11930 | 4/1996 |
| WO | 96/12713 | 5/1996 |
| WO | 96/12721 | 5/1996 |
| WO | 96/16056 | 5/1996 |
| WO | 96/16949 | 6/1996 |
| WO | 96/16961 | 6/1996 |
| WO | 96/17831 | 6/1996 |
| WO | 96/17842 | 6/1996 |
| WO | 96/23784 | 8/1996 |
| WO | 96/23785 | 8/1996 |
| WO | 96/23789 | 8/1996 |
| WO | 96/24596 | 8/1996 |
| WO | 96/29075 | 9/1996 |
| WO | 96/39133 | 12/1996 |
| WO | 97/03068 | 1/1997 |
| WO | 97/08159 | 3/1997 |
| WO | 97/11695 | 4/1997 |
| WO | 97/11945 | 4/1997 |
| WO | 97/11946 | 4/1997 |
| WO | 97/13512 | 4/1997 |
| WO | 97/16446 | 5/1997 |
| WO | 97/17337 | 5/1997 |

| WO | 97/17338 | 5/1997 |
| WO | 97/17343 | 5/1997 |
| WO | 97/18201 | 5/1997 |
| WO | 97/18202 | 5/1997 |
| WO | 97/18203 | 5/1997 |
| WO | 97/18204 | 5/1997 |
| WO | 97/19073 | 5/1997 |
| WO | 97/38692 | 10/1997 |
| WO | 97/41802 | 11/1997 |
| WO | 97/42189 | 11/1997 |
| WO | 97/43281 | 11/1997 |
| WO | 97/45426 | 12/1997 |
| WO | 98/12183 | 3/1998 |
| WO | 98/14433 | 4/1998 |
| WO | 98/15545 | 4/1998 |

OTHER PUBLICATIONS

J.N. Blau, "Migraine: clinical therapeutic, conceptual and research aspects," pp. 4-7, 1987, Chapman and Hall, London, XP 000933853.

Headache Classification Committee of the International Society, "Classification and diagnostic criteria for headache disorders, cranial neuralgia and facial pain," *Cephalalgia* (1988); 8. (Supp. 7): 1-96.

Anthony M. Rasmussen BK. In: Olesen J, Tfelt-Hansen P, Welch KMA (eds), *The Headaches*, New York: Raven Press, Ltd, 1993: 256-257.

Apperley, et al, "Evidence for Two Types of Excitatory Receptor for 5-Hydroxytryptamine in Dog Isolated Vasculature," *British Journal of Pharmacology* 68 (1980): 215-224.

Bouchelet, et al, "Differential Expression of Sumatriptan-Sensitive 5-Hydroxytryptamine Receptors in Human Trigeminal Ganglia and Cerebral Blood Vessels," *Molecular Pharmacology* (1996), 50: 219-223.

M. Gabriella Buzzi and Michael A. Moskowitz, "The antimigraine drug , sumatriptan (GR433175), selectively blocks neurogenic plasma extravasation from blood vessels in dura matter," *British Journal of Pharmacology* (1990), 99: 202-206.

Silberstein SD, Lipton RB, Goadsby PJ (eds), *Headache in Clinical Practice*, Oxford UK: Isis Medical Media Ltd, 1998: 74-77.

J.N. Blau, *Migraine: Clinical, therapeutic, conceptual and research aspects*, London, Chapman and Hall, 1987, pp. 4-7.

Roger K. Cady, *Treating the Headache Patient*, Ch. 6, New York, Marcel Dekker, Inc., 1995, pp. 101-118 and 121-122.

D. Reeves, et al., ANAM V3.11a/96 User's Manual, 1996 Update 1997, pp. 1, 10-14, 16-28, 32-35.

IMITREX Tablets leaflet, Feb. 1997.

* cited by examiner

Fig_1A_

PREEMPTIVE PROPHYLAXIS OF MIGRAINE

CROSS REFERENCES

This application is a continuation-in-part of application Ser. No. 09/185,310, filed 3 Nov. 1998 now U.S. Pat. No. 6,066,092 which claims priority from provisional application 60/064,879 filed Nov. 6, 1997, and a continuation-in-part of PCT Application No. PCT/US99/09414 filed 29 Apr. 1999 and which named the United States as a designated country.

FIELD OF THE INVENTION

The present invention relates generally to the medical field and, more particularly, to a method for predicting the onset of a migraine headache and to a preemptive prophylaxis of the migraine headache.

The preemptive prophylaxis is directed to prevent or reduce the headache phase and/or disability of migraine in humans by the administration of drugs during the prodrome phase of migraine.

BACKGROUND OF THE INVENTION

A headache may be one of several different varieties, each of which has its own unique pain characteristics which differ dramatically. The types of headache include tension, sinus, cluster, rebound and migraine. Migraine is a particularly painful headache that recurs from time to time. The pain is quite severe and often the person with migraine must stay in bed. Dietary, emotional and environmental factors may trigger an attack. On average, migraine sufferers experience an attack per month. Attacks last from four to seventy-two hours. Of interest is that the incidence of migraine appears to be on the rise. Because of the severity and incidence of migraine, prescription medicines have been invented to provide relief.

Migraine sufferers sometimes get a warning signal before the onset of the headache phase of a migraine. The warning signals apparent to the migraineur are classified as aura. The period of aura is preceded by a period classified as prodromal or premonitory period. The periods of aura, prodrome and premonitory are pre-headache. The International Headache Society (IHS) defines aura as neurological symptoms that usually develop over 5–20 minutes and last less than 60 minutes. Headache may occur directly or after an aura free interval of less than 60 minutes. Aura symptoms commonly include, but are not limited to, visual disturbances and numbness or tingling sensations. Less than 20% of patients have migraine with aura (IHS 1.2). See Headache Classification Committee of the International Society. Classification and diagnostic criteria for headache disorders, cranial neuralgia and facial pain. *Cephalalgia* (1988); 8: (Supp. 7): 1–96.

The IHS has defined prodromal symptoms as non-aura symptoms signaling the onset of a migraine attack. The symptoms typically occur a few hours to 48 hours before the onset of the headache phase of the migraine. Headache phase of migraine as used herein means the point in time when head pain is perceived by the sufferer. Prodrome or premonitory symptoms may occur in migraine with (IHS 1.1) and migraine without aura (IHS 1.2). The IHS prefers the term premonitory symptoms over prodrome due to historical use of prodrome to describe aura. Prodrome symptoms as used herein is synonymous to premonitory symptoms. See Headache Classification Committee of the International Society. Classification and diagnostic criteria for headache disorders, cranial neuralgia and facial pain. *Cephalalgia* (1988); 8: (Supp. 7): 1–96.

Prodrome or premonitory symptoms may have physical and mental components. The symptoms have been classified by clinical presentation as excitatory and inhibitory symptoms. Excitatory symptoms include, but are not limited to, irritability, euphoria (being 'high'), physical hyperactivity, excessive yawning, excessive sleepiness, increased sensitivity to light and sound, and craving for foods. Inhibitory symptoms include, but are not limited to, depression, mental withdrawal, behaviour sluggishness, feeling tired, poor concentration, muscle weakness, anorexia and fluid retention. See Headache Classification Committee of the International Society. Classification and diagnostic criteria for headache disorders, cranial neuralgia and facial pain. *Cephalalgia* (1988); 8: (Supp. 7): 1–96 and Anthony M, Rasmussen B K. In: Olesen J, Tfelt-Hansen P, Welch K M A (eds). *The Headaches*. New York: Raven Press, Ltd, 1993: 256–257. Prodrome/premonitory symptoms have been estimated to occur in up to 88% of migraine patients. See supra, Rasmussen.

$5\text{-}HT_1$ receptor agonists have been found useful in the treatment of migraine. $5\text{-}HT_1$ receptors are located, for example, in the dog saphenous vein and the $5HT_1$ receptor agonists with which the present invention is concerned contract the dog saphenous vein. Such compounds may therefore be identified by their contractile effect on the dog isolated saphenous vein strip as described, for example, by Apperley et al, Br. J. Pharmacol, 68, 215–224 (1980). Compounds which are selective $5HT_1$ receptor agonists have also been found to selectively constrict the carotid arterial bed of the anaesthetized dog.

Much work has been done in attempts to identify the subclasses of $5HT_1$ receptors which are implicated in migraine. It is currently thought that $5HT_{1B}$ (formerly $5HT_{1D\beta}$), $5HT_{1D}$ (formerly $5HT_{1D\alpha}$) and $5HT_{1F}$ receptors are particularly important. Tests in isolated cerebral arteries can be used to determine which of these receptor sub-types mediate the action of $5HT_1$ agonist compounds, for example as described in Bouchelet, I. et al, Mol. Pharmacol 1996, 50, 219–223.

Some $5HT_1$ agonists, including $5HT_{1D}$ and $5HT_{1F}$ agonists have also been found to inhibit the trigeminal nerve. This can be assessed by measuring plasma protein extravasation in the dura mater following trigeminal nerve stimulation and administration of labeled albumin; active compounds produce inhibition of dural plasma protein extravasation in this model, which is described in Buzzi. M. G and Moskowitz M. A, Br. J. Pharmacol, 1990 99, 202–206.

A variety of compounds have been identified in the art as $5HT_1$ agonists, for example by selective constriction of the dog isolated saphenous vein or constriction of the carotid arterial bed of the anaesthetized dog. These include indole derivatives such as those disclosed inter alia in: published British Patent Specification Nos. 2082175, 2081717, 2083463, 2124210, 2150932, 2162522, 2168347, 2168973, 2185020, 2186874, 2191488, 2008646, 2289464, 2289465, 2286185; published U.S. Pat. Nos. 5,288,748, 5,317,103, 5,382,592, 5,385,928, 5,387,593, 5,418,236, 5,433,915, 5,451,584, 5,466,688, 5,468,768, 5,519,025, 5,545,644, 5,602,128, 5,618,948, 5,637,611, 5,837,715; published German Patent Specification Nos. 4414113, 4226527; published French Patent Specification Nos. 2699918, 2707294, 2737723; published Japanese Patent Specification Nos.

05320157, 06041071, 07097370, 07109265; published European Patent Specification Nos. 147107, 237678, 242939, 244085, 225726, 254433, 303506, 313397, 354777, 382570, 464558, 506363, 506369, 450238, 451022, 451008, 478954, 438230, 494774, 497512, 501568, 580539, 581538, 586866, 590970, 590971, 603432, 610134, 620222, 620223, 644187, 641787, 645385, 648767, 666258, 668273, 683155, 700905, 703229, 707007, 708102, 712837, 714894, 714896, 729958, 733628, 736525, 747353, 749962, 755932, 768301, 810220; and published International Patent Application Nos. WO92/11013, WO92/11014, WO92/06973, WO93/00086, WO92/13856, WO93/00094, WO91/18897, WO93/00333, WO94/02460, WO94/02477, WO94/03446, WO94/06789, WO94/10171, WO94/11363, WO94/11356, WO94/13620, WO94/14773, WO94/14772, WO94/14771, WO94/14770, WO94/15930, WO94/14779, WO94/18193, WO94/21619, WO94121611, WO94/21610, WO94/20466, WO94/24127, WO94/29293, WO95/01334, WO95/01965, WO95/05383, WO95/05381, WO95/05366, WO95/06636, WO95/11903, WO95/20588, WO95121167, WO95/21166, WO95/28933, WO95/32196, WO96/04274, WO96/04269, WO96/06846, WO96/06638, WO96/09288, WO96/11195, WO96/11930, WO96/11923, WO96/11685, WO96/12721, WO96/12713, WO96/16056, WO96/17842, WO96/17831, WO96/16961, WO96/16949, WO96/23789, WO96/23784, WO96/23785, WO96/24596, WO96/29075, WO96/39133, WO97/41802, WO97/03068, WO97/08159, WO97/11695, WO97/13512, WO97/11946, WO97/11945, WO97/17343, WO97/17338, WO97/17337, WO97/18204, WO97/18203, WO97/18202, WO97/18201, WO97/16446, WO97/19073, WO97/38692, WO97/43281, WO97/42189, WO97/45426, WO95/14004, WO98/12183, WO98/14433, WO98/15545. The compounds disclosed in the aforementioned specifications (hereinafter described as "Y compounds") are described as being useful in the treatment of migraine and cluster headache. Some are also claimed to be useful in treating tension-type headache.

Specific examples of 5HT$_1$ agonist Y compounds include those indole derivatives often called "triptans" such as the compounds with the generic names: sumatriptan, naratriptan, rizatriptan, zolmitriptan, eletriptan, almotriptan and frovatriptan. Other examples of 5HT$_1$ agonist Y compounds include those commonly known as ALX-0646, LY334370, U109291, 1S159 and PNU-142633.

Sumatriptan is marketed inter alia in the U.S. as IMITREX® (sumatriptan succinate) Tablets, IMITREX® (sumatriptan succinate) Injection and IMITREX® (sumatriptan) Nasal Spray. In many other countries sumatriptan products are marketed as IMIGRAN®, rather than IMITREX®.

IMITREX® (sumatriptan succinate) Tablets are indicated for the acute treatment of migraine attacks with or without aura in adults. IMITREX® (sumatriptan succinate) Tablets are not approved for the prophylactic therapy of migraine or for use in the management of hemiplegic or basilar migraine. IMITREX® Tablets contain sumatriptan (as its succinate salt), a selective 5HT$_1$ receptor subtype agonist. Sumatriptan succinate is chemically designated as 3-[2-(dimethylamino) ethyl]-Nmethyl-indole-5-methanesulfonamide succinate (1:1), and it has the structure shown in formula (I):

The empirical formula is $C_{14}H_{21}N_3O_2S \cdot C_4H_6O_4$, representing a molecular weight of 413.5. IMITREX® (sumatriptan succinate) Tablets are, for example, disclosed and/or claimed in U.S. Pat. No. 4,816,470, U.S. Pat. Nos. 5,037,845 and 5,863,559, which are incorporated by reference herein.

IMITREX® (sumatriptan succinate) Injection is indicated for (1) the acute treatment of migraine attacks with or without aura and (2) the acute treatment of cluster headache episodes. IMITREX® (sumatriptan succinate) Injection is not approved for use in the management of hemiplegic or basilar migraine. The name, structural formula, empirical formula and molecular weight of sumatriptan succinate are as hereinbefore described. IMITREX® (sumatriptan succinate) Injection is, for example, disclosed and/or claimed in U.S. Pat. No. 4,816,470 and U.S. Pat. No. 5,037,845, which are incorporated by reference herein.

IMITREX® (sumatriptan) Nasal Spray is indicated for the acute treatment of migraine attacks with or without aura in adults. IMITREX® (sumatriptan) Nasal Spray is not intended for the prophylactic therapy of migraine or for use in the management of hemiplegic or basilar migraine. IMITREX® (sumatriptan) Nasal Spray contains sumatriptan, a selective 5-hydroxytryptamine$_1$ receptor subtype agonist. Sumatriptan is chemically designated as 3-[2-(dimethylamino)ethyl]-N-methyl-1H-indole-5-methanesulfonamide, and it has the structure shown in Formula (II):

The empirical formula is $C_{14}H_{21}N_3O_2S$, representing a molecular weight of 295.4. Due to the presence of sulphuric acid in the nasal spray formulation, the hemisulphate salt of sumatriptan is formed in situ. IMITREX® (sumatriptan) Nasal Spray is, for example, disclosed and/or claimed in U.S. Pat. No. 4,816,470, U.S. Pat. No. 5,037,845, U.S. Pat. No. 5,705,520 and U.S. Pat. No. 5,554,639, which are incorporated by reference herein.

Naratriptan is marketed inter alia in the United States as AMERGE® (naratriptan hydrochloride) Tablets. In many other countries, the trade mark NARAMIG® is used instead of AMERGE®. AMERGE® Tablets are indicated for the acute treatment of migraine attacks with or without aura in adults. AMERGE® Tablets are not approved for the prophylactic therapy of migraine or for use in the management of hemiplegic or basilar migraine. AMERGE® (naratriptan hydrochloride) Tablets contain naratriptan as its hydrochloride salt. Naratriptan hydrochloride is a selective 5HT$_1$ receptor subtype agonist. It is chemically designated as N-methyl-3-(1-methyl-4-piperidinyl)-1H-indole-5-ethanesulfonamide monohydrochloride, and it has the structure shown in formula (III):

The empirical formula is $C_{17}H_{25}N_3O_2S \cdot HCl$, representing a molecular weight of 371.93. AMERGE® (naratriptan hydrochloride) Tablets are, for example, disclosed and/or claimed in U.S. Pat. No. 4,997,841, which is incorporated by reference herein.

Rizatriptan is marketed inter alia in the United States as MAXALT® (rizatriptan benzoate) Tablets and MAXALT-MLT™ (rizatriptan benzoate) Orally Disintegrating Tablets. MAXALT® (rizatriptan benzoate) Tablets and MAXALT-MLT™ (rizatriptan benzoate) Orally Disintegrating Tablets are indicated for the acute treatment of migraine attacks with or without aura in adults. MAXALT® (rizatriptan benzoate) Tablets and MAXALT-MLT™ (rizatriptan benzoate) Orally Disintegrating Tablets are not approved for the prophylactic therapy of migraine or for use in the management of hemiplegic or basilar migraine. MAXALT® (rizatriptan benzoate) Tablets and MAXALT-MLT™ (rizatriptan benzoate) Orally Disintegrating Tablets contain rizatriptan benzoate, a selective $5\text{-HT}_{1B/1D}$ receptor agonist. Rizatriptan benzoate is described chemically as: N,N-dimethyl-5-(1H-1,2,4-triazol-1-ylmethyl)-H-indole-3-ethanamine monobenzoate. Its empirical formula is $C_{15}H_{19}N_5 \cdot C_7H_6O_2$, representing a molecular weight of the free base of 269.4. MAXALT® (rizatriptan benzoate) Tablets are, for example, disclosed and/or claimed in U.S. Pat. No. 5,298,520 and U.S. Pat. No. 5,602,162, which are incorporated by reference herein. MAXALT-MLT™ (rizatriptan benzoate) Orally Disintegrating Tablets are, for example, disclosed and/or claimed in U.S. Pat. No. 4,305,502, U.S. Pat. No. 4,371,516, U.S. Pat. No. 4,758,598, U.S. Pat. No. 5,298,520 and U.S. Pat. No. 5,602,162, which are incorporated by reference herein.

Zolmitriptan is marketed inter alia in the United States as ZOMIG™ (zolmitriptan) Tablets. ZOMIG™ (zolmitriptan) Tablets are indicated for the acute treatment of migraine with or without aura in adults. ZOMIG™ (zolmitriptan) Tablets are not approved for the prophylactic therapy of migraine or for use in the management of hemiplegic or basilar migraine. ZOMIG™ (zolmitriptan) Tablets contain zolmitriptan, which is a selective $5\text{-HT}_{1B/1D}$ receptor agonist. Zolmitriptan is chemically designated as (S)-4-[[3-[2-(Dimethylamino)ethyl]-1H-indol-5-yl]methyl]-2-oxazolidinone. The empirical formula is $C_{16}H_{21}N_3O_2$, representing a molecular weight of 287.36. ZOMIG™ (zolmitriptan) Tablets are disclosed and/or claimed in U.S. Pat. No. 5,466,699, which is incorporated by reference herein.

Other $5\text{HT}_1$ agonists in development include eletriptan, frovatriptan, almotriptan, ALX-0646, LY334370, U109291, IS159 and PNU-142633.

The above mentioned anti-migraine agents have not been approved for the prevention of migraine. In fact, the current product label for each of these agents states that they are not intended for prophylactic therapy of migraine, e.g., AMERGE® (naratriptan hydrochloride) Tablets. Clinically, these agents are used at the onset of the headache phase of the migraine, (CMAJ 1997; 156:1273–1287.), and are commonly reserved for the treatment of severe migraine pain. (Silberstein S D, Lipton R B, Goadsby P J (eds). *Headache in Clinical Practice*. Oxford UK: Isis Medical Media Ltd, 1998, 74–77.) Thus, it would be desirable to provide an anti-migraine agent useful for the prevention of the headache phase of the migraine. It would be further desirable to be able to predict the onset of migraine before the head pain actually occurs and thereby permit the prophylactic administration of medicine.

The Automated Neuropsychological Assessment Metrics (ANAM) is a set of standardized batteries of cognitive tests, modified by neuropsychologists in the U.S. Armed Forces for precise measurement of cognitive processing efficiency of military personnel. The tests assess sustained concentration and attention, mental flexibility, spatial processing, cognitive processing efficiency, mood, arousal/fatigue level, and short-term, long-term and working memory. The ANAM is now in the public domain. The most recent version is ANAM V3.lla/96 which includes the following battery of tests:

1. Subject Demographics Form
2. Stanford Sleepiness or Sleep/Fatigue Scale
3. Mood Scale 2
4. Simple and Two-Choice Reaction Time
5. Sternberg Memory Search Tasks
6. Running Memory Continuous Performance Task
7. Mathematical Processing Task
8. Digit Set Comparison Task
9. Logical Reasoning-Symbolic
10. Tower of Hanoi (Tower Puzzle)
11. Stroop Color/Word Interference
12. Code Substitution (Letter/Symbol Comparison)
13. Code Substitution (Immediate and Delayed Recall)
14. Spatial Processing Task (Simultaneous)
15. Matching to Sample
16. Tapping (Left and Right Index Finger)
17. Modified Orientation and Amnesia Test It would be desirable to be able to use a subset of these tests to predict the onset of migraine before the head pain actually occurs and thereby permit the prophylactic administration of medicine.

The present invention is directed to meeting one or more of the above-stated desirable objectives.

SUMMARY OF THE INVENTION

The present invention provides a method of preventing the headache phase of migraine in a human comprising administration of a $5\text{HT}_1$ agonist to said human exhibiting prodrome symptoms of migraine. Suitably, the method comprises administration of a headache phase preventing effective amount of the $5\text{HT}_1$ agonist.

In a second aspect, the invention provides a $5\text{HT}_1$ agonist for use in the manufacture of a medicament for administration to a human exhibiting prodrome symptoms of migraine in order to prevent the headache phase of migraine.

According to a third aspect, the invention provides a pharmaceutical composition comprising a $5\text{HT}_1$ agonist as active ingredient for administration to a human exhibiting prodrome symptoms of migraine in order to prevent the headache phase of migraine.

In the second and third aspects, suitably a headache phase-preventing effective amount of a $5\text{HT}_1$ agonist is administered. In preferred embodiments of the first, second and third aspects, the effective amount is from about 0.25 to 100 mg.

The $5\text{HT}_1$ agonist employed in accordance with the first, second and third embodiment is typically administered orally, parenterally, by inhalation, intranasally or rectally. Parenteral, and oral administration are preferred, with oral administration being particularly preferred.

Suitably, the $5\text{HT}_1$ agonist administered to said human exhibiting prodrome symptoms of migraine is selected from the group consisting of sumatriptan, naratriptan, rizatriptan, eletriptan, zolmitriptan, frovatriptan, almotriptan, ALX-0646, LY334370, U109291, IS159 and PNU-142633. It is preferably selected from the group consisting of sumatriptan, naratriptan, rizatriptan, zolmitriptan, eletriptan, frovatriptan and almotriptan. Sumatriptan and naratriptan are particularly preferred, with sumatriptan being especially preferred.

When the $5HT_1$ agonist is sumatriptan, a headache phase-preventing effective amount is typically from about 2 mg to 100 mg. If the sumatriptan is administered subcutaneously, a headache phase-preventing amount is suitably from about 2 mg to 6 mg. For oral administration, a suitable headache phase-preventing amount is 25 mg to 100 mg. When sumatriptan is administered intranasally, a suitable headache phase-preventing amount is in the range 5 mg to 20 mg. A suitable headache phase-preventing amount of sumatriptan for rectal administration is in the range 12.5 mg to 25 mg.

When the $5HT_1$ agonist is naratriptan, a headache phase-preventing effective amount is typically from about 0.25 mg to 2.5 and suitably from 1 mg to 2.5 mg.

When the $5HT_1$ agonist is rizatriptan, a typical headache phase-preventing effective amount is from about 1 mg to 10 mg, suitably 5 mg to 10 mg.

When the $5HT_1$ agonist is zolmitriptan, and a typical headache phase-preventing effective amount is from about 0.5 mg to 5 mg, suitably 1 to 5 mg.

When the $5HT_1$ agonist is eletriptan, a typical headache phase-preventing effective amount is from about 5 mg to 80 mg, suitably 20 mg to 80 mg.

When the $5HT_1$ agonist is frovatriptan, a typical headache phase-preventing effective amount is from about 1 mg to 40 mg, suitably 2.5 mg to 40 mg.

When the $5HT_1$ agonist is almotriptan, a headache phase-preventing effective amount is from about 2 mg to 150 mg, suitably 12.5 mg to 25.

The present invention further provides a preemptive prophylaxis migraine method using the following cognitive tests: Simple Reaction Time; Running Memory Continuous Performance Task; Matching to Sample; Mathematical Processing Task; and interpreting the results as a percent of baseline indicator of need for prophylaxis. Preferably the tests are administered in the listed sequence. Advantageously the tests are preceded by the Stanford Sleepiness Scale and Mood Scale 2 tests.

In a preferred arrangement there is provided a preemptive prophylaxis migraine device including a microprocessor having a memory, a battery of tests loaded into the memory of the microprocessor and including a Simple Reaction Time, a Running Memory Continuous Performance Task, a Matching to Sample, and a Mathematical Processing Task; means for computing the score on a trial of these tests to establish a baseline and for storing the baseline in the memory; the means for computing being operative for computing the score of a subsequent trial of the tests and comparing the same to the stored baseline; and means for indicating a cognitive change.

In another aspect, the invention provides a method of preventing the headache phase of migraine in a human comprising administration of an over-the-counter or non-prescription medicine to said human exhibiting prodrome symptoms of migraine.

In another aspect of the invention, a method is provided for preventing the headache phase of migraine in a human comprising administration of a Cox-2 inhibitor to said human exhibiting prodrome symptoms of migraine.

These and other objects, aspects, features and advantages of the present invention will become apparent from the following detailed description when taken in conjunction with the referenced drawings.

BRIEF DESCRIPTION OF THE DRAWINGS

Reference is now made more particularly to the drawings which illustrate the best presently known mode of carrying out the invention and wherein similar reference characters indicate the same parts throughout the views.

The accompanying drawings illustrate two devices and one method for carrying out the present invention and wherein.

DETAILED DESCRIPTION

Figure 1:
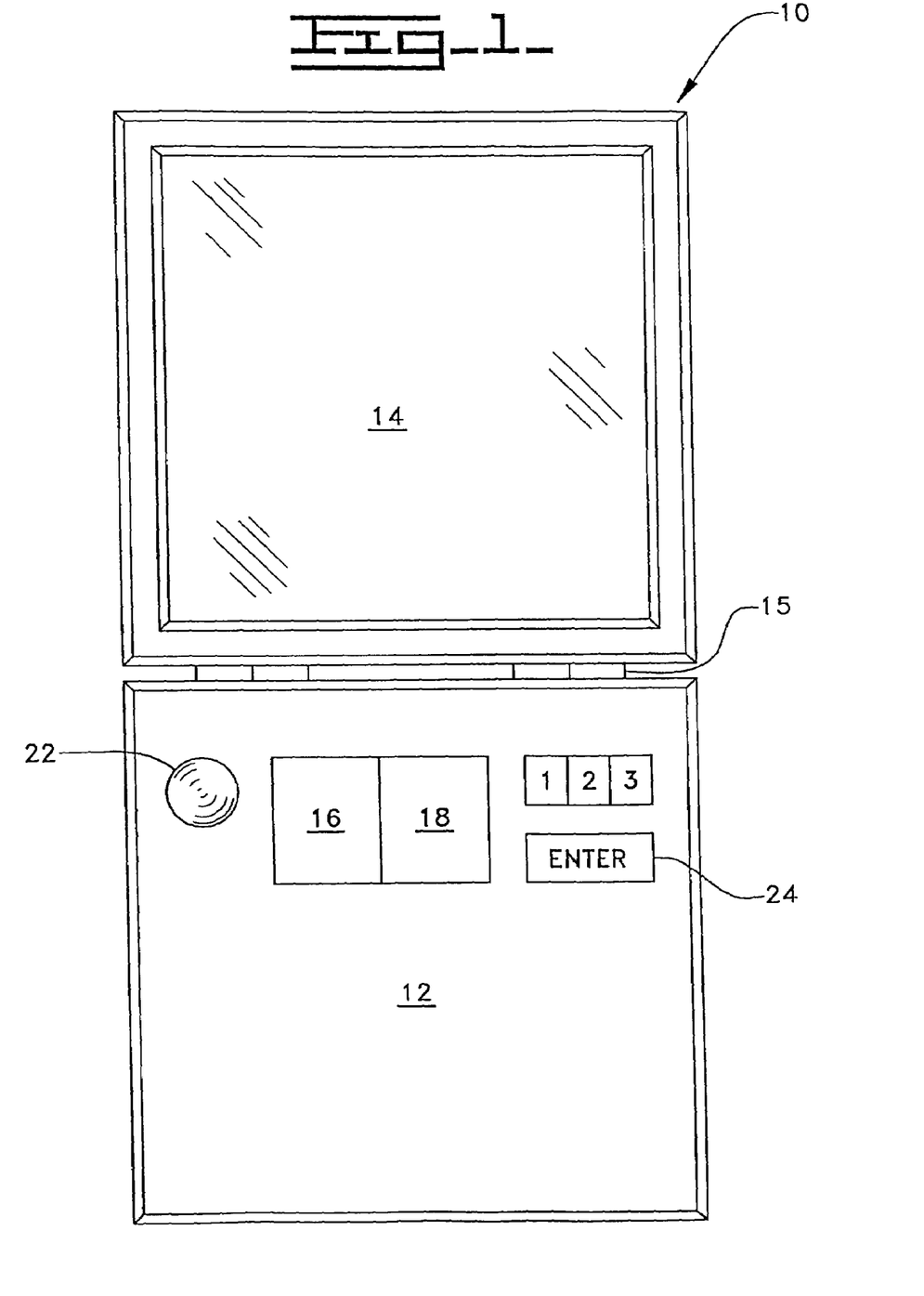
FIG. 1 is a plan view of a hand-held computer which is one apparatus for determining cognitive change in a human.

FIG. 1 shows a preemptive prophylaxis of migraine device in the form of a hand-held computer, generally designated 10, and having a key pad 12 and a screen 14 which advantageously is at least four inches (10.16 cm.) square. A hinge 15 is provided so the screen 14 may be conveniently folded down upon the key pad 12 for storage or transporting. When open the computer 10 is conveniently about 5"×9" (12.7 cm. by 22.86 cm.) in size. The key pad 12 has a built-in set of two mouse buttons 16,18, a start/stop or on/off button 22, an enter key 24, and Mood Scale 2 keys 1, 2 and 3. As used herein the terms "buttons" and "keys" are intended to mean the same thing. The computer 10 contains memory chips (not shown) which have a set of programmed cognitive tests 103–106 (hereafter described) and which record a person's performance time in milliseconds on those tests. The computer program uses the score in milliseconds on the third trial of these cognitive tests as a baseline measurement, which is converted to a stanine score. Subsequent trials are similarly scored and converted to stanine.

Figure 1A:
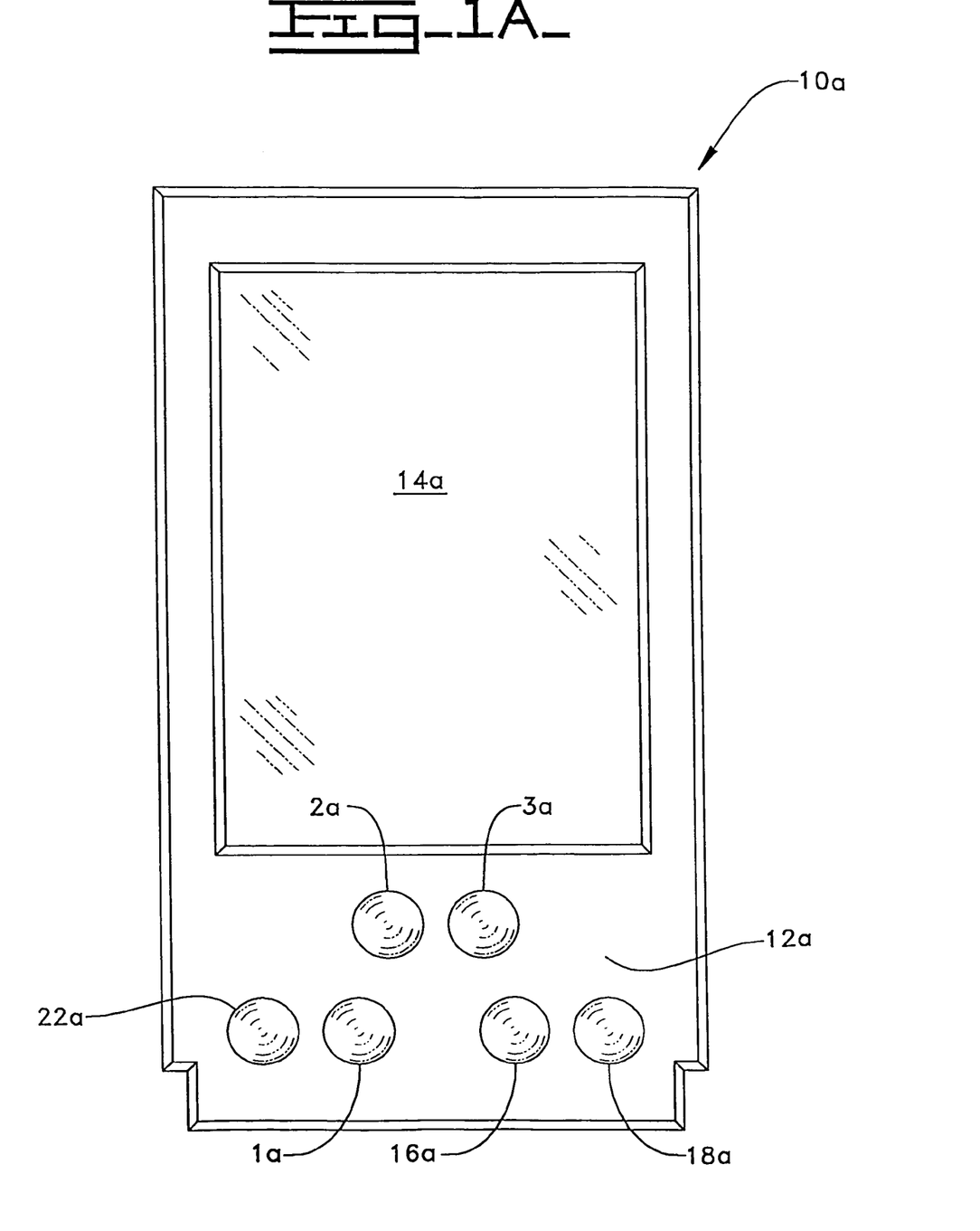
FIG. 1A is a plan view of a palm-top type computer which is another apparatus for determining cognitive change in a human.

FIG. 1A shows a palm-top type computer 10a which, when programmed with the cognitive tests 103–106, performs the same functions as hand-held computer 10. Accordingly, the same functional parts identified in FIG. 1, are identified in FIG. 1A with the same numerals and the letter "a". Further description is deemed unnecessary. It is believed that the largest palm-top computer now available is 7.8 inches (19.81 cm.) long and the screen 14a is not as large as the desired four inches (10.16 cm.) square. However, this deficiency is offset by the savings in using mass produced devices.

Figure 2:
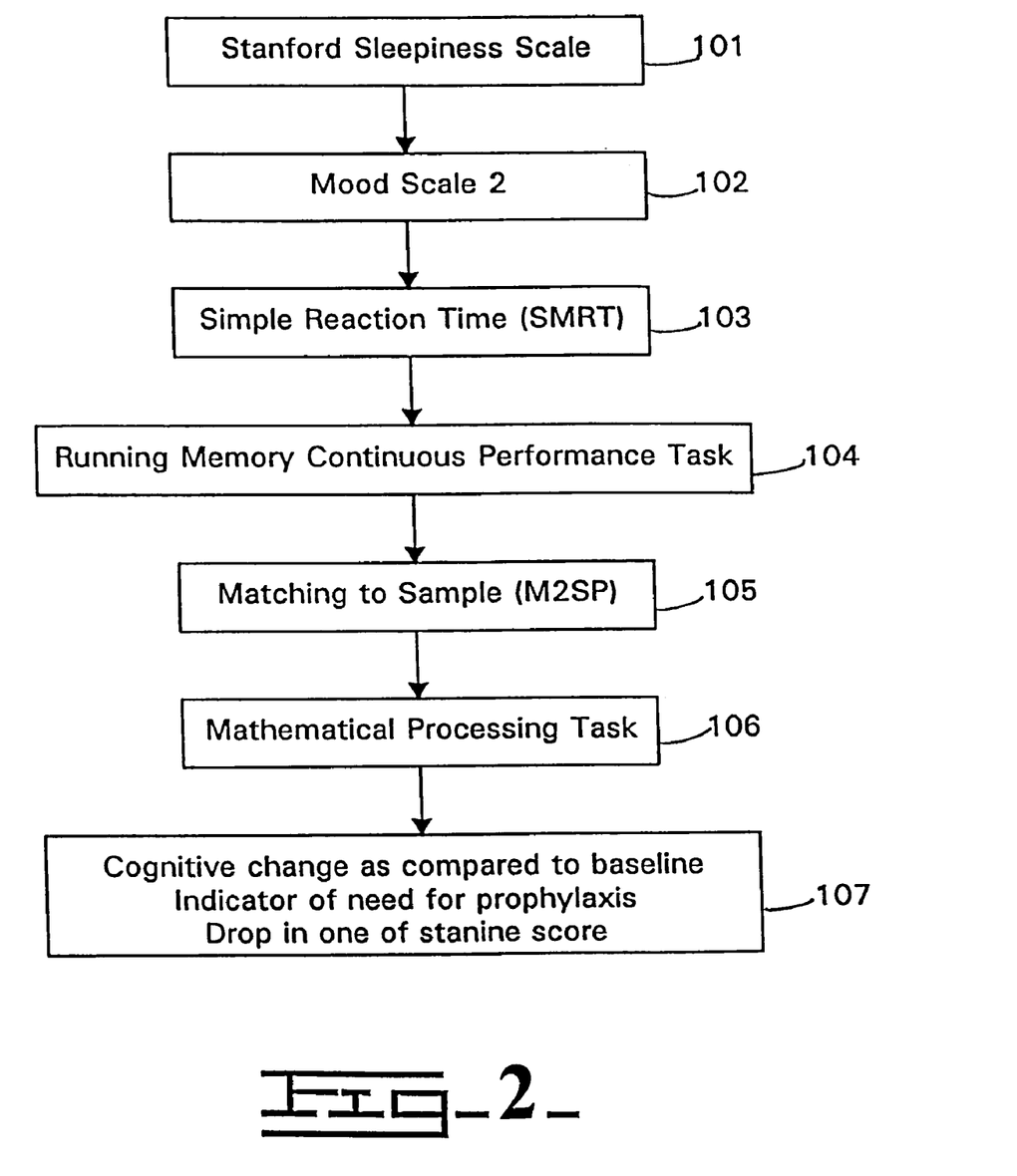
FIG. 2 is a flow chart illustrating the steps and sequence of a method for performing preemptive prophylaxis of migraine.

FIG. 2. shows the sequence of the method. From the seventeen tests of the original ANAM, four subtests were selected and sequenced for measuring cognitive processing efficiency of migraine sufferers, as follows:

1. Simple Reaction Time (SMRT), 103
2. Running Memory Continuous Performance Task (CPT), 104
3. Matching to Sample (M2SP), 105
4. Mathematical Processing Task (MATH), 106.

Also included are two preliminary measures of alertness and mood that are also part of the ANAM:

1. Stanford Sleepiness Scale, 101
2. Mood Scale 2, 102.

DESCRIPTION OF SUBTESTS

1. The first step 101 is Stanford Sleepiness Scale which consists of seven statements that describe the present state of alertness or sleepiness and are numbered from one to seven, with one being highly alert and seven being close to sleep. Individuals rate their level of alertness prior to taking the first subtest of the battery. It provides a way to monitor fatigue over the course of repeated measures. Subjective ratings may be correlated with measured performance.
2. The second step 102 is Mood Scale 2 which consists of a list of thirty-six adjectives that are rated on a three-point scale. Using mouse button 16 participants respond to each adjective by indicating "yes," "moderately," or "no," based on how they feel at the present time. The Mood Scale 2 categories include anger, happiness, fear (anxiety), depression, activity, and fatigue.
3. The third step 103 is Simple Reaction Time (SMRT) which presents a simple stimulus on the screen (*). In response, the individual presses the mouse button 16 each time the stimulus appears. The Reaction Time measures the speed of the motor response, the peripheral nerve conduction velocity. This represents the "hardware" of the nervous system in terms of input, followed by motor response. Actual cognitive processing time is not involved in this test.
4. The fourth step 104 is Running Memory Continuous Performance Test (CPT) which is a continuous letter comparison task. A randomized sequence of upper-case letters, A through Z, is presented one at a time in the center of the computer screen 14. The person presses button 16 if the letter on the screen matches the letter that immediately preceded it; and different button 18 if the letter on the screen is different than the immediately preceding letter. The task lasts approximately five minutes. The CPT was specifically designed to assess components of memory, attention, efficiency and consistency. This task is forced paced, with individuals having only a brief time in which to respond.
5. The fifth step 105 is Matching to Sample (M2SP) and consists of a number of trials that begins with a first design being presented in the center of the screen 14 for three seconds, followed by a showing that contains two designs. The person matches one of the two designs with the first design or sample by pressing the appropriate button 16 or 18. The design is a 4×4 checkerboard and varies by the number of cells that are shaded from one cell through twelve cells.
6. The sixth step 106 is Mathematical Processing (MATH) and involves arithmetic problems presented in the middle of the screen 14. Working from left to right, the person solves the addition and subtraction and decides if the answer is greater or less than the number 5.

As indicated, the scores are recorded by the computer 10 and the score on the third trial of these sequenced cognitive tests 103-106 are used as the baseline measurement. Subsequent trials measure cognitive change as compared to baseline. A drop of one in stanine score is an indicator of the onset of migraine and an indicator of need for prophylaxis. See FIG. 2, 107. This was empirically determined by the following research. The preemptive prophylaxis of migraine method was used to measure cognitive deficiency during a migraine in each of a group of ten migraineurs. The method was used to measure the return of cognitive efficiency after injection of sumatriptan, an anti-migraine medication, in each of the group of ten migraineurs. The method measured cognitive change, compared to the baseline stanine score, that predicted the onset of a migraine.

The above described preemptive prophylaxis of migraine device and method allows a migraine sufferer to take medication to preempt the occurrence of head pain, associated symptoms and accompanying disability.

It will be appreciated that the precise dose of a $5HT_1$ agonist administered to prevent the headache phase of migraine may depend on the particular compound used, the age and condition of the patient and the frequency and route of administration and will be at the ultimate discretion of the attendant physician. The compound may be administered in single or divided doses and may be administered one or more times, for example 1 to 3 times per day during exhibition of prodrome symptoms of migraine.

Also, a compound for use according to the invention may be formulated in a conventional manner using one or more pharmaceutically acceptable excipients. Thus, a compound for use according to the invention may for example be formulated for oral, sub-lingual, buccal, parenteral, rectal or intranasal administration or in a form suitable for administration by inhalation or insufflation (either through the mouth or nose).

For oral administration the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Preferred tablet formulations of sumatriptan are those described in European Patent No. 0503440.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl P-hydroxybenzoates or sorbic acid).

For buccal administration, the compositions may take the form of tablets or lozenges formulated in conventional manner.

A compound for use according to the method may be formulated for parenteral administration by injection, conveniently intravenous, in intramuscular or subcutaneous injection. Formulations for injection may be presented in unit dosage form e.g., in ampoules or in multi-dose containers, optionally with an added preservative.

The compositions for parenteral administration may take such forms as suspensions, solutions or emulsions in oily or aqueous vehicles, and may contain formulatory agents such as suspending, stabilizing and/or dispersing agents. Alternatively, the active ingredient may be in dry form such as a powder, crystalline or freeze-dried solid for constitution with a suitable vehicle, e.g., sterile pyrogen-free water or isotonic saline before use. They may be presented, for example, in sterile ampoules or vials.

A compound for use according to the method may also be formulated in rectal compositions such as suppositories or retention enemas, e.g., containing conventional suppository bases such as cocoa butter or other glyceride. Preferred compositions for rectal administration are those described in European Patent No. 0639072, which is incorporated by reference herein.

Tablets for sub-lingual administration may be formulated in any conventional manner.

For intranasal administration a compound for use according to the invention may be used, for example, as a liquid in the form of a spray or drops or as a powder. Suitably the preparation for intranasal administration is delivered in the form of a spray or aerosol from an insufflator or from a pressurized pack or nebulizer with the use of a suitable propellant. Preferably sumatriptan is administered intranasally in the form of its hemisulphate salt in a composition as described in European Patent No. 0490689, which is incorporated by reference herein.

For administration by inhalation the compound for use according to the invention is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges, e.g., of gelatin, for use in an inhaler or insufflator may be formulated containing a powder mix of a compound of use in the invention and a suitable powder base such as lactose or starch.

The method will now be further illustrated with reference to the following non-limiting examples.

BIOLOGICAL EXAMPLES

An open label pilot study was conducted to determine whether oral naratriptan 2.5 mg taken as a single dose during the prodrome could prevent the onset of the headache phase of migraine. Results of the study suggest that administration of 2.5 mg naratriptan during prodrome was effective in preventing the onset of the headache phase of migraine.

Twenty patients recruited at 4 study sites were administered oral naratriptan 2.5 mg after onset of prodrome symptoms for a total of 63 prodromes. Sixty percent of the treated prodromes did not progress to headache. The pain severity of headaches that were not prevented were reduced as compared to baseline pain severity of migraine attacks not treated with naratriptan.

An additional 13 patients recruited at a fifth site were also treated. All 13 patients reported headache following each treatment. Upon review, all 13 patients reported onset of headache within 3 hours after administration of naratriptan. Eighty-seven percent of prodromes in this patient group were treated $\leq 2$ hours before onset of headache. A similar finding was seen at the remaining 4 sites where 15 of the 25 headaches (60%) that were not prevented occurred $\leq 2$ hours after treatment. This data suggests these patients waited too late to administer naratriptan and may be due to the fact that patients were instructed to record the onset of premonitory symptoms, but were asked to delay treatment until they were sure a migraine headache was imminent. These data were considered independent of the data from the other 4 sites due to the dichotomy of response as compared to the 4 sites in which the response rates ranged from 58% to 66%.

Figure 3:
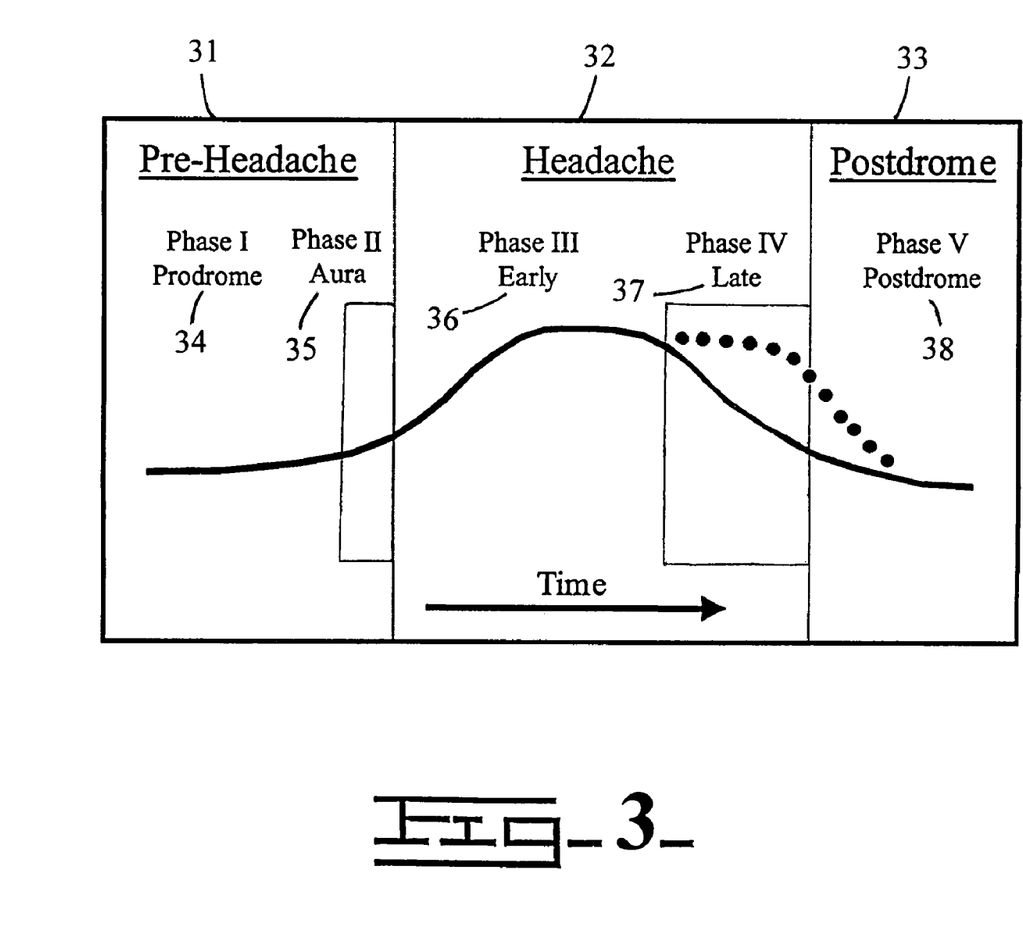
FIG. 3 is a chart illustrating the therapeutic phases of migraine and including the treatment options most suitable to each phase of migraine.

FIG. 3 shows the phases of migraine. The entire migraine event is roughly divided into three time periods: pre-headache 31, headache 32 and postdrome 33. These time periods are further divided into phases. The pre-headache period is composed of Phase I, prodrome 34, and Phase II, aura 35. The headache period is divided into Phase III, early headache 36, and Phase IV, late headache 37. Finally, Phase V, postdrome 38, encompasses the entire postdrome period.

During the prodrome phase 4 of migraine, identified in FIG. 3, there are alternatives to the use of $5HT_1$ agonists to preclude the onset of the headache phase. Advantageously, these alternatives include over-the-counter (OTC) or non-prescription drugs such as acetylsalicylic acid (aspirin); the combination of 4'-hydroxyacetanilide, acetylsalicylic acid, and caffeine (e.g., Excedrin®); and other non-narcotic analgesics as the anti-migraine medication. Nonsteroidal anti-inflammatory drugs (NSAIDs) are also effective as an alternative to $5HT_1$ agonists during prodrome. Examples of suitable NSAIDs include ibuprofen and other NSAIDs (e.g. acetominophen, naproxen, indomethacin) which inhibit both COX-1 and COX-2 enzymes, and wholly COX-2 inhibitors such as celecoxib, sold under the brand name Celebrex®, and rofecoxib, sold under the brand name Vioxx®. These so-called COX-2 inhibitors operate by inhibiting the COX-2 enzyme, which triggers symptoms of pain and inflammation, while leaving the COX-1 enzyme, which aids in maintaining the stomach lining, unaffected. As used herein, the term "COX-2 inhibitor" means an inhibitor which operates on the COX-2 enzyme and not the COX-1 enzyme. U.S. Pat. No. 6,048,850, the disclosure of which is herein incorporated by reference, describes one method of COX-2 inhibitor operation.

Other objects, features and advantages of the present invention will be apparent to those skilled in the art. While preferred medications, uses and steps of the method have been illustrated and described, this had been by way of illustration and the invention should not be limited except as required by the scope of the appended claims.

We claim:

1. A preemptive prophylaxis migraine method for preventing the headache phase of a primary migraine disorder including the steps of: determining prodromal symptoms of migraine; and administering an anti-migraine medication, wherein the step of determining prodromal symptoms of migraine includes performing cognitive tests to determine prodromal symptoms of migraine.

2. A preemptive prophylaxis migraine method as set forth in claim 1, wherein the step of performing cognitive tests includes performing a simple reaction time test, a running memory continuous performance test, a matching to sample test, and a mathematical processing test.

3. A preemptive prophylaxis migraine method as set forth in claim 2, wherein the step of performing cognitive tests is preceded by the steps of performing a Stanford sleepiness scale test and a mood scale test.

4. A preemptive prophylaxis migraine method as set forth in claim 1, including the step of administering and scoring the cognitive tests by a computer, and storing the scores received on the cognitive tests in the computer.

5. A preemptive prophylaxis migraine method as set forth in claim 4, including converting the stored scores from the cognitive tests into a stanine score.

6. A preemptive prophylaxis migraine method as set forth in claim 5, including comparing the stanine score to a baseline score, and indicating when there is a difference between the baseline and the stanine score as indicative of the onset of the prodromal symptoms of migraine.

7. A preemptive prophylaxis migraine method as set forth in claim 1, wherein the step of administering an anti-migraine medication includes administering a $5HT_1$ agonist as the anti-migraine medication.

8. A preemptive prophylaxis migraine method as set forth in claim 7, wherein the $5HT_1$ agonist is selected from the group consisting of sumatriptan, naratriptan, rizatriptan, zolmitriptan, eletriptan, frovatriptan and almotriptan.

9. A preemptive prophylaxis migraine method for reducing occurrence of the headache phase of a primary migraine disorder in a human comprising the steps of: determining prodromal symptoms of migraine in the human; and administering a migraine headache phase-preventing amount of a $5HT_1$ agonist to the human exhibiting the prodromal symptoms of migraine, wherein the step of determining prodromal symptoms of migraine includes performing cognitive tests to determine prodromal symptoms of migraine.

* * * * *